US008452371B2

(12) United States Patent
Feldman et al.

(10) Patent No.: US 8,452,371 B2
(45) Date of Patent: May 28, 2013

(54) ARTERY IMAGING SYSTEM (75) Inventors: Charles L. Feldman, Marblehead, MA (US); Peter Stone, Boston, MA (US); Ahmet U. Coskun, Brighton, MA (US)

(73) Assignees: The Brigham and Women's Hospital, Inc., Boston, MA (US); Northeastern University, Boston, MA (US)

( * ) Notice: Subject to any disclaimer, the term of this patent is extended or adjusted under 35 U.S.C. 154(b) by 518 days.

(21) Appl. No.: 11/680,977

(22) Filed: Mar. 1, 2007

(65) Prior Publication Data

US 2008/0004530 A1 Jan. 3, 2008

Related U.S. Application Data (60) Provisional application No. 60/777,999, filed on Mar. 1, 2006.

(51) Int. Cl.
*A61B 5/05* (2006.01)

(52) U.S. Cl.
USPC ........... 600/407; 600/437; 600/450; 600/463; 600/443

(58) Field of Classification Search
USPC .......................... 600/437, 463, 443, 407, 450
See application file for complete search history.

(56) References Cited

U.S. PATENT DOCUMENTS

| 5,485,845 | A | 1/1996 | Verdonk et al. |
| 5,771,895 | A | 6/1998 | Slager |
| 6,059,731 | A | 5/2000 | Seward et al. |
| 6,375,615 | B1 | 4/2002 | Flaherty et al. |
| 7,366,563 | B2 * | 4/2008 | Kleen et al. ................... 600/424 |
| 7,480,398 | B2 | 1/2009 | Kleen et al. |
| 2005/0196028 | A1 * | 9/2005 | Kleen et al. ................... 382/128 |
| 2005/0197559 | A1 * | 9/2005 | Boese et al. .................. 600/407 |

FOREIGN PATENT DOCUMENTS

| JP | 2005-253963 | 9/2005 |
| WO | WO02/064011 | 8/2002 |
| WO | WO2005/111932 | 11/2005 |

OTHER PUBLICATIONS

Paul Schoenhagen and Steven Nissen, Heart Online, Understanding Coronary Artery Disease: Tomographic Imaging with Intravascular Ultrasound, Heart 2002; 88; pp. 91-96, 7 pages.

Adrian F. Low, et al., Technology Insight: Optical Coherence Tomography—Current Status and Future Development, Nature Clinical Practice Cardiovascular Medicine, Mar. 2006 vol. 3 No. 3, 9 pages.

(Continued)

*Primary Examiner* — Unsu Jung
*Assistant Examiner* — Joel Lamprecht
(74) *Attorney, Agent, or Firm* — Fish & Richardson P.C.

(57) ABSTRACT

Techniques for imaging a blood vessel are described. A transducer attached to a catheter is guided to a first site within a blood vessel. The catheter is moved to a second site proximal to the first site at a speed selected to enable the transducer to generate a signal indicative of a geometry wall, the lumen, and a portion of the side branch. A first image of the blood vessel obtained from the signal is oriented with a second image of the blood vessel such that a first portion of the first image aligns with a second portion of the second image.

18 Claims, 10 Drawing Sheets

OTHER PUBLICATIONS

Pedro R. Moreno, M.D. and James E. Muller, M.D., Detection of High-Risk Atherosclerotic Coronary Plaques by Intravascular Spectroscopy, Journal of Interventional Cardiology, vol. 16, No. 3, 2003, pp. 243-252.

Sergio Waxman, et al. Detection and Treatment of Vulnerable Plaques and Vulnerable Patients: Novel Approaches to Prevention of Coronary Events, Circulation Journal of The American Heart Association, 2006; 114; pp. 2390-2411.

The International Search Report and the Written Opinion of the International Searching Authority, for PCT/US2007/063069, mailed Jun. 3, 2008.

Supplementary Partial European Search Report in Application No. 07 75 7718, dated Dec. 7, 2009.

Wahle et al., "Geometrically Correct 3-D Reconstruction of Intravascular Ultrasound Images by Fusion with Biplane Angiography—Methods and Validation", IEEE Trans. on Medical Imaging, v. 18(8) (Aug. 1999).

English translation of Office Action issued in copending Japanese Application No. 2008-557496, issued by the Japan Patent Office.

* cited by examiner

ARTERY IMAGING SYSTEM

CROSS-RELATED APPLICATION

Under 35 U.S.C. 119(e)(1), this application claims the benefit of provisional application Ser. No. 60/777,999, entitled "Artery Imaging System," filed Mar. 1, 2006.

TECHNICAL FIELD

The invention relates generally to imaging an artery and more particularly to reconstructing the luminal boundary of the coronary artery.

BACKGROUND

Atherosclerosis is a condition in which fatty deposits called plaque collect along the walls of arteries. The accumulation of plaque can erode the wall of the artery, diminish its elasticity (stretchiness), and interfere with blood flow. A rupture of the plaque can cause the formation of a blood clot that blocks the flow of blood through the artery, leading a heart attack or a stroke. Clots can also form around the plaque deposits, further interfering with blood flow and posing added danger if they break off and travel to the heart, lungs, or brain.

Clinical studies of atherosclerosis often rely on angiography to produce an image of the luminal border of a blood vessel of interest and intravascular ultrasound (IVUS) to obtain images of the plaque and the luminal wall from an ultrasonic transducer inserted within the blood vessel. Although IVUS provides detailed images of the lumen, vessel wall, and plaque, it yields no information about the specific location or absolute orientation of the image. Current techniques for determining the absolute orientation of an IVUS image take advantage of the irregularities of the lumen (i.e., bumps and crevices) that appear in both the IVUS image and the angiogram. With these techniques, the IVUS image is rotated relative to the angiogram until a correlation between the irregularities in both the angiogram and the IVUS image reaches a maximum. The matching of the irregularities may be inexact due in part to ambiguities in the images and to some of the irregularities changing over time.

SUMMARY

In an aspect, the application features a method and a computer readable medium for imaging a blood vessel. The method includes guiding a transducer attached to a catheter inserted into the blood vessel to a first site within the blood vessel, where the first site is distal to a region of interest that has a side branch joined to the wall. The catheter is moved to a second site proximal to the first site at a speed selected to enable the transducer to generate a signal indicative of a geometry of the wall, the lumen, and a portion of the side branch. A first image of the blood vessel obtained from the signal is orientated with a second image of the blood vessel such that a first portion of the first image aligns with a second portion of the second image, where the first and second portions correspond to the side branch.

In another aspect, the application features an apparatus for generating an image of a blood vessel. The apparatus includes a catheter for insertion into the blood vessel. The catheter includes a transducer configured to generate a signal indicative of a geometry of the wall, a lumen defined by the wall, and a portion of a side branch joined to the wall. The apparatus also includes a circuit coupled to the transducer, where the circuit is configured to construct a first image of the blood vessel from the signal and to orient the first image relative to a second image of the blood vessel such that a first portion of the first image aligns with a second portion of the second image, the first and second portions corresponding to the side branch.

Embodiments may include one or more of the following. While moving the catheter to the second site, the transducer may direct energy (e.g., acoustic energy or electromagnetic energy) towards the wall of the blood vessel and detect echoes resulting from energy reflected from the wall. For example, the transducer may be an acoustic transducer or an electromagnetic transducer. The transducer may be configured to rotate about the catheter. The transducer may include an array of piezoelectric elements disposed about the periphery of the catheter, and the transducer being further configured to illuminate the wall with a rotating beam of energy.

Frames showing portions of the wall may be generated and the first image may be constructed from the frames. Constructing the first image from the frames may include selecting a first subset of the frames, where the first subset includes frames acquired at times separated by an integer number of heart cycles, and stacking successive frames from the first subset to form a cast of the blood vessel. Relative orientations between the successive frames from the first subset may be adjusted to account for relative motion resulting from movement of the catheter. The second image may be obtained using angiography and may show a three dimensional cast of a luminal boundary of the blood vessel.

The transducer may be guided using real-time angiograms showing at least a portion of the catheter inside the lumen. The pullback speed of the catheter may be selected such that the signal generated by the transducer includes information for generating at least one image showing a portion of the side branch. A controller may be used to guide the catheter through the blood vessel to the first site and move the catheter to the second site within the blood vessel.

The details of one or more embodiments are set forth in the accompanying drawings and the description below. Other features, objects, and advantages will be apparent from the description and drawings, and from the claims.

DETAILED DESCRIPTION

An image of a blood vessel, such as a coronary artery, may be constructed by an imaging system that combines traditional angiography techniques (e.g., X-ray or computed tomography) with one or more intravascular imaging techniques, in which a catheter is inserted into the blood vessel to be imaged. Angiography produces an image, called an angiogram, showing the borders of the blood vessel lumen, including certain side branches. An angiogram can take the form of either a three-dimensional "cast" or a two-dimensional silhouette-like image. Examples of catheter-based techniques that can be combined with angiography include intravascular ultrasound imaging (IVUS), optical coherence tomography (OCT), near-infrared spectroscopy (NIR), intravascular magnetic resonance imaging (MRI), and other catheter-based imaging techniques.

IVUS, OCT, and NIR are all performed by inserting a catheter having one or more transducers into the blood vessel and moving the catheter through the vessel until the transducers are positioned within a region of the vessel to be imaged, referred herein to as the "region of interest." Angiograms showing the catheter inside the blood vessel may be used to guide the catheter through the vessel. The catheter is then pulled through the vessel, thus drawing transducers through the region of interest. As it traverses the region of interest, the transducer transmits energy toward the wall of the vessel and detects any resulting echoes. For example, IVUS uses ultrasound transducers that transmit and receive acoustic energy as ultrasonic pulses, while OCT and NIR use electromagnetic transducers to direct electromagnetic energy toward and receive electromagnetic energy from the wall. The transducer encodes the echoes as electric signals, which are subsequently analyzed by a computer with reference to an electrocardiogram to generate images of the vessel wall and lumen within the region of interest.

In some intravascular MRI techniques, an RF coil located in the catheter obtains images of the vessel wall while the patient is placed in an external magnet. In other intravascular MRI techniques, all of the components required for MRI measurement, including RF coils, magnets, and detectors are located in the catheter.

While catheter-based imaging techniques can produce high quality "intravascular images" of the lumen and inside wall of the blood vessel, these techniques typically provide inadequate information regarding the location of the image or its absolute spatial orientation (i.e., its orientation with respect to the patient's coordinate system). To determine the absolute orientation of an intravascular image (e.g., an IVUS image), one overlays the intravascular image on the angiogram such that one or more fiducial features (e.g., side branches) appearing in the intravascular image align with corresponding fiducial features appearing in the angiogram. This process of matching the fiducial features (e.g., side branches) of the intravascular image to the corresponding fiducial features in an angiogram often estimates the absolute orientation of the intravascular images more accurately than approaches in which one maximizes a correlation between irregularities in an angiogram and corresponding irregularities in an IVUS image. The improved accuracy arises in part because fiducial features (e.g., side branches) tend to remain substantially unchanged over time and are easily recognizable in both the angiogram and intravascular image.

Figure 1:
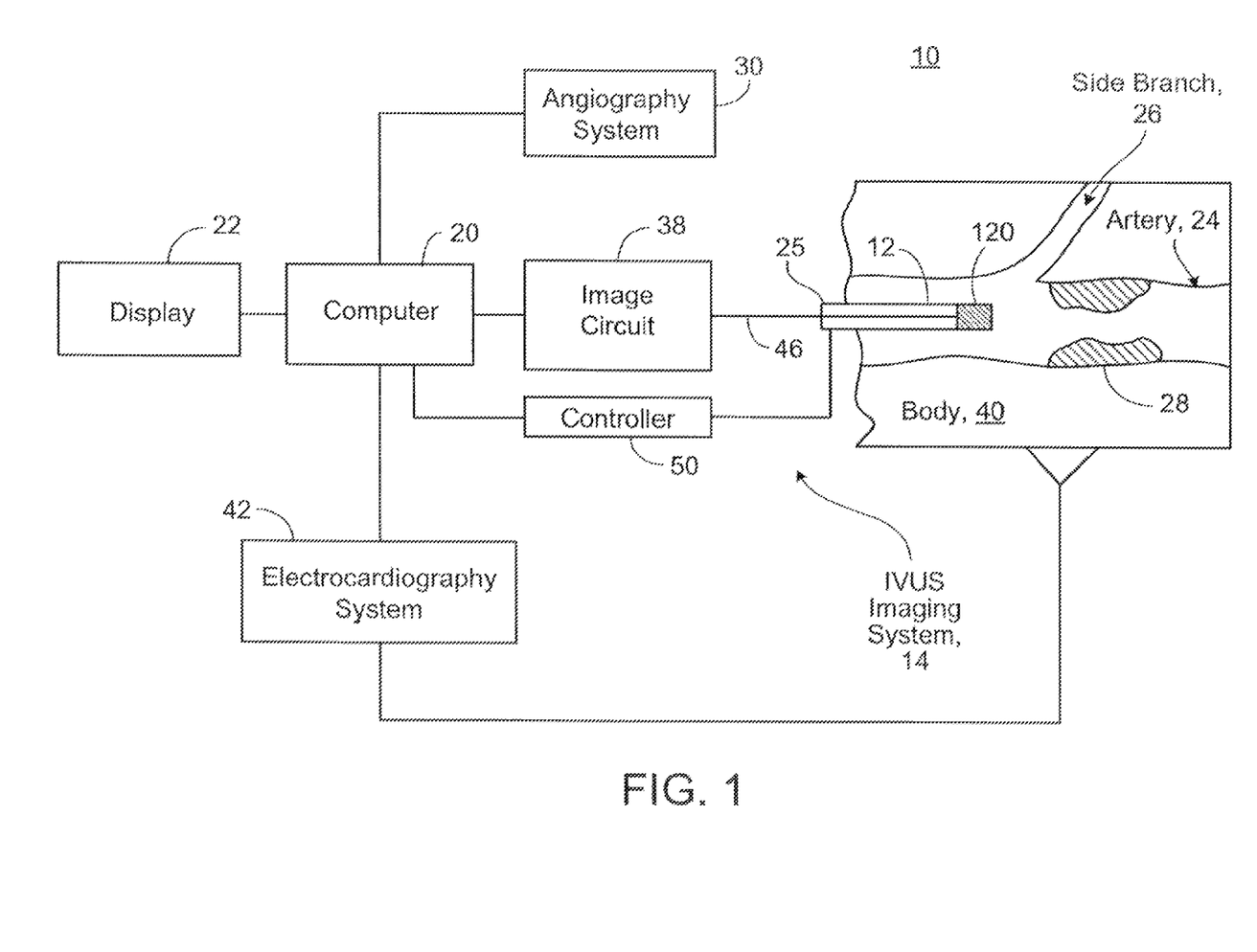
FIG. 1 is a block diagram of a system for imaging a blood vessel.

FIG. 1 is an overall block diagram of an imaging system 10 for imaging an artery 24 of a body 40 using angiography and IVUS imaging. Other catheter-based intravascular imaging techniques, such as those described above, could be used instead of or in addition to IVUS. For ease of explanation, examples using angiography and IVUS are described in detail.

The imaging system 10 includes an IVUS imaging system 14, an angiography imaging system 30, an electrocardiography system 42, a controller 50, and a computer 20 in data communication with the IVUS imaging system 14, the angiography system 30, and the electrocardiography system 42, and the controller 50. The computer 20 is coupled to a display 22 on which images of the artery 24 are presented to a skilled practitioner. The IVUS imaging system 14 includes a catheter 12 configured to be inserted into the artery 24, a transducer 120 secured to the distal end of the catheter 12 for imaging plaque 28 deposited on the interior wall of the artery 24, a controller 50 that attaches to the catheter 12 and moves the catheter 12 through the artery 24, and an image circuit 38 (e.g., a processor) electrically coupled to the transducer 120 by an electrical conductor 46 (e.g., a wire). The controller 50 includes a motor that may controlled by a processor within the controller 50 and/or by the computer 20. As described above, the IVUS imaging system 14 shown in FIG. 1 could be replaced with or modified to include other catheter-based intravascular imaging systems, such as OCT, NIR, and intravascular magnetic resonance imaging (MRI) systems.

The transducer 120 produces ultrasound having a frequency within a range of approximately 10 MHz and 150 MHz in response to receiving electrical control signals generated by the image circuit 38. The ultrasound generated by the transducer 120 results in acoustic echoes reflected from the plaque 28 and the walls of artery 24. The transducer 120 converts the echoes to electrical signals, which are detected and amplified by the image circuit 38 and subsequently processed by the computer 20. In some embodiments, the transducer 120 includes a single rotating transducer that is switched back and forth between a transmission mode and a receiving mode. In other embodiments, the transducer 120 includes an array of piezoelectric elements disposed about the periphery of the catheter 12, and configured to rotate a beam of ultrasound around the interior of the artery 24. In some of these embodiments, the transducer 120 includes an array of thirty-two piezoelectric elements arranged about the circumference of the catheter 12 with each element having dimensions approximately 0.1 mm by 0.5 mm and with the catheter 12 having a diameter of approximately 1 mm. Such an array has a radial resolution better than 0.1 mm and a longitudinal resolution of 0.2 mm when imaging a vessel having a 2 mm luminal diameter. To improve the radial resolution, so that small lipid rich regions or small tears in the intima are captured in an image, it may be necessary to increase the frequency of the ultrasound, possibly with some sacrifice in penetration depth of the ultrasound.

The angiography system 30 produces an angiogram of the artery 24 that shows the borders of the arterial lumen, including one or more side branches 26 of the artery 24. In some embodiments the angiogram is a three-dimensional cast, and in other embodiments the angiogram is a two-dimensional silhouette. The angiography system 30 can be any system capable of generating a contrast image of the artery 24 and the side branch 26. Examples of the angiography system 30 include X-ray, magnetic-resonance imaging, and computed tomography angiography systems. The angiography system 30 may include circuitry and software for generating a three-dimensional image of the artery 24 from two or more two-dimensional images. An example of a system with this capability is the Allura 3D-CA X-ray angiography system available from Philips, Inc. In some embodiments, the angiograms system 30 produces a series of motion picture frames or a "movie" of the artery 24. Each frame can be converted to a digital frame and stored in a memory of the computer 20. The movie may be viewed in real time on the display 22 as the angiography is being performed, or reviewed later using recall from digital memory.

The electrocardiography system 42 produces an electrocardiogram indicative of the positions of the heart at known times over the cardiac cycle. By analyzing the electrocardiogram, the computer 20 references the angiograms and IVUS images to corresponding positions of the heart and selects from those, for analysis, those images occurring at times when the heart is at the same position in the cardiac cycle. Images that are referenced to a particular time are referred to as "frames". Preferably, the computer 22 selects only those images occurring at times when the heart is essentially stopped momentarily at the end of diastole. Such selections of "diastolic frames" reduce inaccuracy arising from the motion of the heart. At the computer 20, the electrical signals from the image circuit 38, the angiograms received from the angiography imaging system 30, and electrocardiogram generated by the electrocardiography system 42 are processed to generate images of the arterial lumen, including a portion of the side branch 26.

Figure 2:
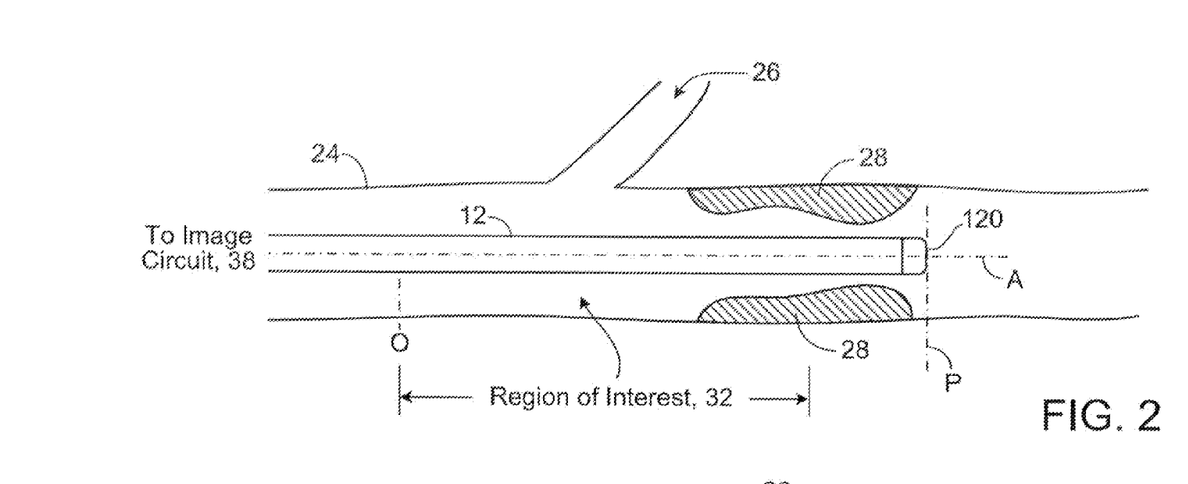
FIGS. 2 and 3 are schematic views of a catheter positioned to image a blood vessel.

As shown in more detail in FIG. 2, IVUS images are obtained by inserting the catheter 12 into the artery 24 and advancing the catheter 12 along a guide wire (not shown) through the artery 24 until the transducer 120 is positioned within a region of the artery 24 to be imaged. This region, which lies between points O and P, is referred to as the "region of interest 32." The catheter 12 may be guided manually or under the control of the controller 50. Angiograms showing the catheter 12 inside the artery 24 are used to guide the catheter 12 through the artery 24 such that the catheter 12 is disposed within the artery 24 with the transducer 120 positioned proximally to the side branch 26 and opposite a portion of a stenotic lesion or plaque 28 at point P. In some embodiments, the computer 20 directs the controller 50 to move the catheter 12 to the point P based on angiograms that the computer 20 receives from the angiography system 30. The transducer 120 is positioned to transmit a beam of ultrasonic pulses transverse to the longitudinal axis A of catheter 12.

The artery 24 may be any artery. In some applications, the artery to be imaged is a coronary artery. The diameter of the artery 24 typically ranges between approximately 1 mm and 5 mm and the diameter of the side branch 26 typically ranges between approximately 0.75 mm and 2.50 mm. Although only one side branch 26 is shown within the region of interest 32, additional side branches could join the artery 24 within the region of interest 32. The artery 24 may be another type of blood vessel, e.g., a vein.

Figure 3:
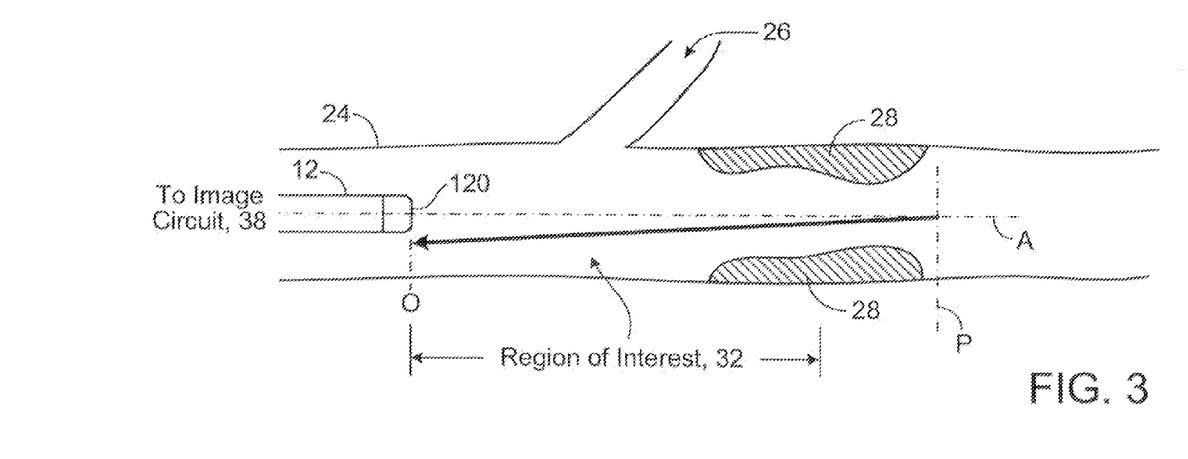

As shown in FIG. 3, guided by angiograms produced by angiography system 30, the practitioner pulls the catheter 12 through the artery 24 such that the transducer 120 moves through the region of interest, past the side branch 26, until it reaches the proximal edge of the region of interest at point O. Alternately, the controller 50 may be used to pull the catheter 12 at a constant, preset speed. As it moves the transducer 120 transmits a rotating beam of ultrasonic pulses toward the wall of the artery 24 and transverse to the longitudinal axis A of the catheter 12 such that the beam irradiates a circular path around the interior of the artery 24. These ultrasonic pulses pass into the wall and through the plaque 28, which is inside the wall, until they reach the outer portion of wall of the artery 24. The wall, including the plaque and the outer portion of the wall, reflects the pulses toward the transducer 120 as acoustic echoes. The transducer 120 detects the acoustic echoes, encodes them as electrical signals, and transmits them back along conductor 46 to the image circuit 38. These signals represent a set of data for each position at which the acoustic echoes are detected by the transducer 120. The image circuit 38 amplifies the electrical signals received from the transducer 120 and transmits the amplified signals to the computer 20. In some embodiments, the image circuit 38 constructs images from the signal that show the plaque constituents and the outer wall of the artery. The image circuit 38 may also filter and further process the electrical signals before transmitting them to the computer 20.

To image the portions of the side branches of the vessel, the catheter 12 is pulled through the artery 24 at a pullback speed that is slow enough to provide the transducer 120, as it moves through the artery 24, with sufficient time to detect echoes reflected from the side branches. The pullback speed is adjusted to enable at least one frame to capture a portion of the side branch 26, though it is preferable to obtain two or more frames that capture a portion of the side branch 26. In some embodiments, a pullback speed of less than 0.5 mm/s enables the transducer 120 to generate at least one frame that captures a portion of the side branch 26, and a pullback speed ranging between 0.2 and 0.3 mm/s enables the transducer 120 to generate at least two frames that capture a portion of the side branch 26. For example, if a typical patient's heart rate is approximately 60 beats per minute (i.e., one beat per second), the transducer 120 captures one diastolic frame every second as it is pulled through the artery 24. If the diameter of one side branch 26 is approximately 1 mm to 1.5 mm, a pullback speed of less than 0.5 mm/s enables the transducer 120 to capture one frame showing the opening of the branch 26 or in some cases, the two frames showing the edges of the opening of the branch 26. A pullback speed of 0.25 mm/s guarantees at least 2-3 frames showing the branch 26. Although slowing the pullback speed produces more frames showing the branch 26, thus leading to higher quality IVUS images of the branch 26, from a clinical point of view, it is desirable to reduce the time the catheter 12 is disposed within the artery 24, both to improve patient tolerance to the procedure and to minimize the risks of damaging the artery and other risks that are generally associated with the invasiveness of the procedure. For example, if the region of interest 32 has a length of approximately 5-7 cm, at a pullback speed of approximately 0.5 mm/s the total travel time required for the transducer to traverse the region of interest 32 approximately 2 minutes. Reducing the pullback speed by a factor of two to approximately 0.25 mm/s doubles the total time to approximately 4 minutes. At present, clinical guidelines recommend that the catheter 12 be disposed in the artery 24 for no longer than approximately 4-5 minutes. Based on these guidelines, a practical pulling speed typically ranges between 0.2 and 0.3 mm/s for traversing a distance between approximately 5 and 7 cm, though any speed slow enough to yield at least one frame showing a portion of the side branch 26 could be used.

The pull-back procedures described in FIGS. 2 and 3 with respect to IVUS could also be employed in other catheter-based intravascular imaging techniques, such as those described above.

Figure 4A:
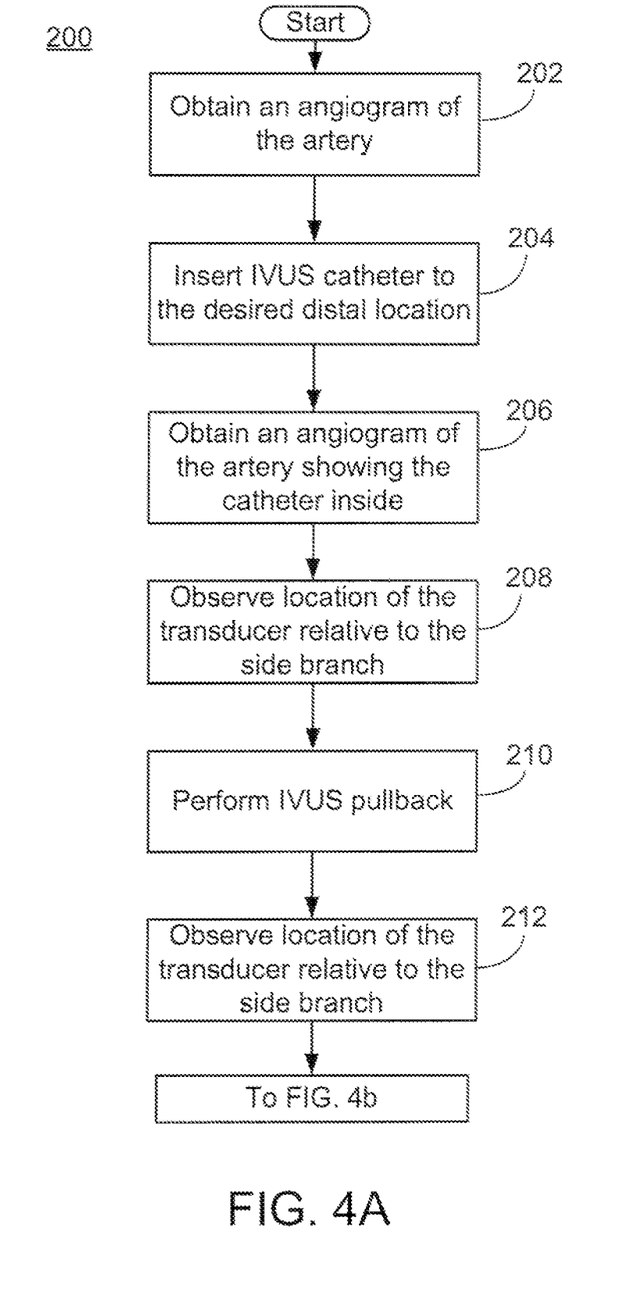
FIGS. 4a-c collectively show a flowchart of a process for imaging a blood vessel using the system shown in FIG. 1.
Figure 4B:
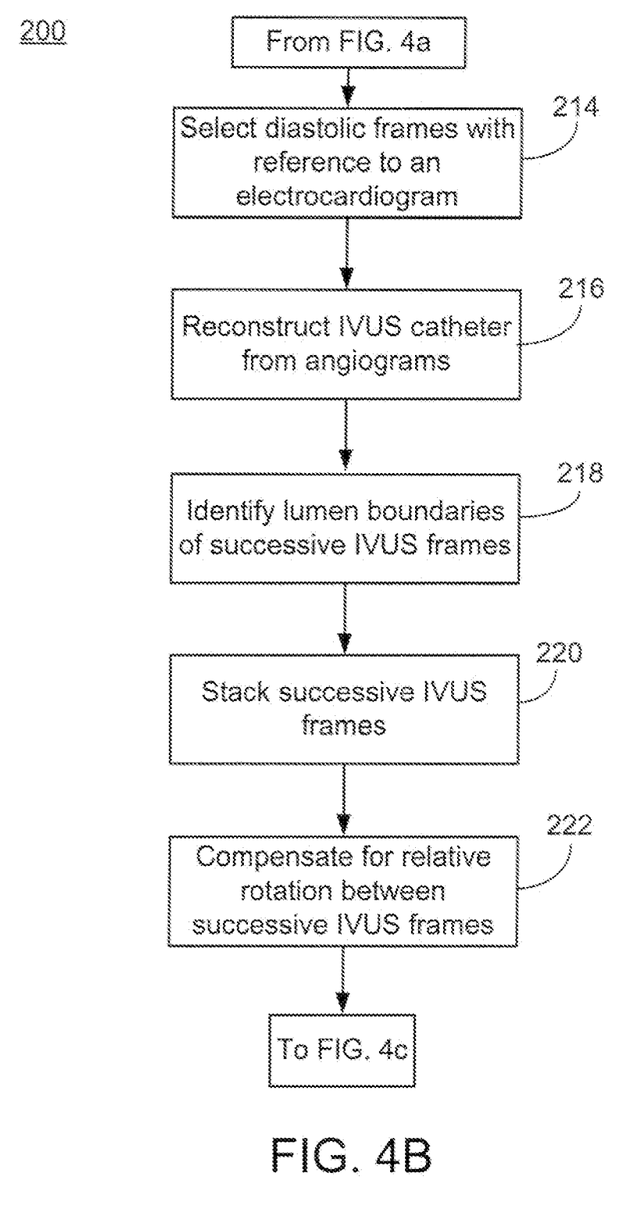

FIGS. 4a-b describe a process 200 for imaging the artery 24 using the imaging system 10 shown in FIG. 1. For ease of explanation, the process 200 is described with respect to IVUS only. However, the process 200 could employ other catheter-based intravascular imaging techniques, such as those described above, in place of or in addition to IVUS.

Initially, the angiography imaging system 30 produces an angiogram showing a three dimensional cast of the luminal boundary of the artery 24 (step 202). The luminal boundary is the interface between the blood and the portion of the artery 24 (i.e., the endothelium) that contacts the blood. In some embodiments, the imaging system 30 reconstructs the cast from multiple two-dimensional angiograms captured from different planes. The catheter 12 is inserted into the artery 24 and guided to the desired distal location at point P within the region of interest as illustrated in FIG. 2 (step 204). In some embodiments, the catheter 12 is guided using real-time angiography, a procedure often referred to as "fluoro," provided by system 30. This results in an angiogram showing the luminal border of the artery with the catheter inside (step 206). In some embodiments the angiogram is a biplane angiogram constructed from two planar angiograms oriented perpendicular or obliquely with respect to each other and obtained either sequentially or simultaneously. Using angiography, the location of the transducer 120 with respect to the side branch 26 is observed and recorded (step 208). In embodiments in which the artery 24 is a coronary artery, an example of a recorded location is "the left anterior descending artery distal to the second diagonal branch."

Then, in an IVUS pullback procedure, the catheter 12 is pulled through the artery 24 as described above with respect to FIGS. 2 and 3, such that the transducer 120 traverses the region of interest 32 defined between points P and O (step 210). The catheter 12 is pulled with sufficiently slow speed to provide the transducer 120 with sufficient time to detect echoes reflected from the side branch 26 as the catheter 12 moves through the artery 24 past the opening of the side branch 26. The slow pullback enables the system 10 to produce at least one frame showing a portion of the side branch 26. After the transducer 120 has been moved to the point O that is proximal to the region of interest, the IVUS pullback procedure is stopped. Using angiography, the current location of the transducer 120 with respect to the side branch 26 is observed and recorded (step 212). During the previous steps 202, 204, 206, 208, 210, and 212, the subject's electrocardiogram is recorded simultaneously with the angiograms and IVUS images. The frames taken at a time when the heart is at the end of diastole (i.e., diastolic frames) are selected for further processing (step 214). In some embodiments, frames taken at times corresponding to other positions of the heart in a cardiac cycle (e.g., during systole) are selected.

Using angiograms obtained from step 206, the computer 20 reconstructs the catheter 12 in three-dimensional space (step 216). From the diastolic frames, the lumen boundaries of successive diastolic IVUS frames, including the first portion (i.e., the first few millimeters) of the side branch 26 are identified, either automatically, using image processing software or manually by a skilled practitioner (step 218). The computer 20 reconstructs the lumen of the artery 24 by stacking success IVUS diastolic frames together (step 220). During the stacking procedure 220, the frames are placed at corresponding locations on the catheter reconstruction obtained in step 216 and centered along the cross section of the catheter 12 at right angles to the catheter axis A. The relative orientation between successive IVUS frames is corrected to take into account any relative rotation between frames caused by the bending or torsion of the catheter (step 222). A suitable method for determining the correct relative orientation of successive IVUS frames is described in Wahle et al. "Geometrically Correct 3-D Reconstruction of Intravascular Ultrasound Images by Fusion with Biplane Angiography—Methods and Validation," IEEE transactions on Medical Imaging, Vol. 18, No. 8, August 1999, pages 686-699, herein incorporated by reference. The resulting image is a cast of the artery constructed from the IVUS frames, referred to as an "IVUS cast," Although the relative orientation between successive frames are corrected, the absolute orientation of the IVUS cast with respect to the patient's coordinate system remains ambiguous. To determine the absolute orientation of the IVUS cast, the computer 20 overlays the angiogram obtained in step 202 with the IVUS cast (step 224) and orients the IVUS cast such that the portion of the side branch 26 or multiple side branches appearing in the IVUS cast aligns with the corresponding side branch(es) shown in the angiogram.

Figure 5:
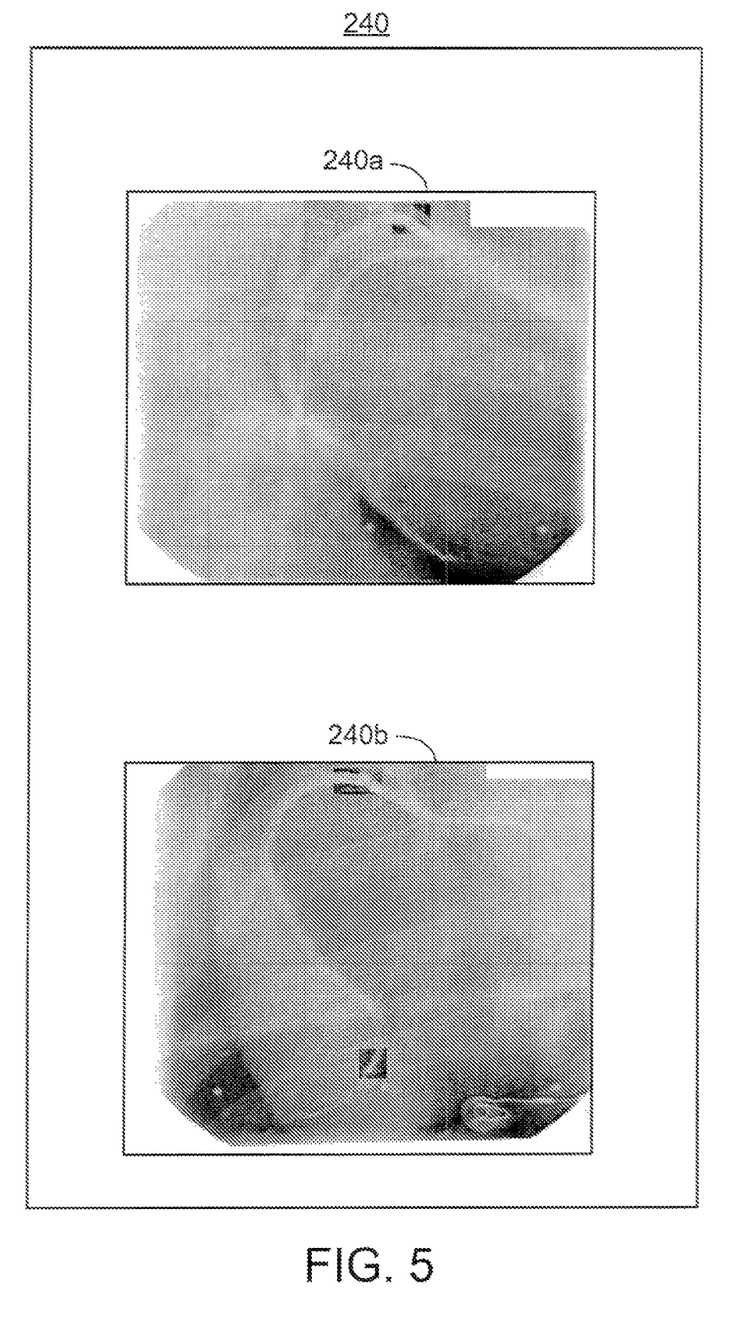
FIG. 5 shows an exemplary biplane angiogram.
Figure 6:
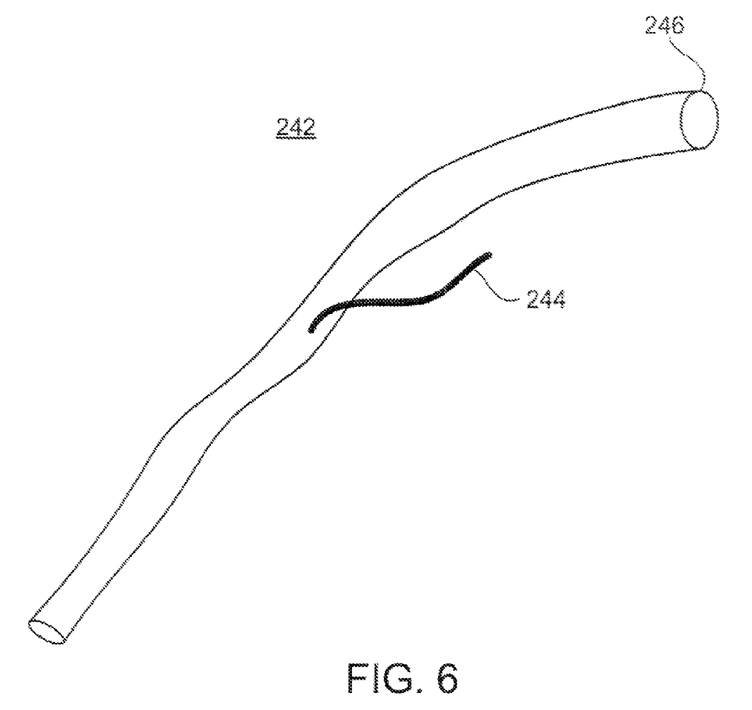
FIG. 6 shows a three-dimensional cast of an artery constructed from a biplane angiogram.

FIG. 5 shows a biplane angiogram 240 showing a right anterior oblique (RAO) view 240a and left anterior oblique (LAO) view 240b from a porcine right coronary artery into which IVUS catheter has been inserted. Dilute contrast is used to make it is possible to see the IVUS core and the lumen simultaneously. FIG. 6 shows a three-dimensional cast 242 of an artery 246 and its side branch 244 obtained using biplane angiography.

Figure 7:
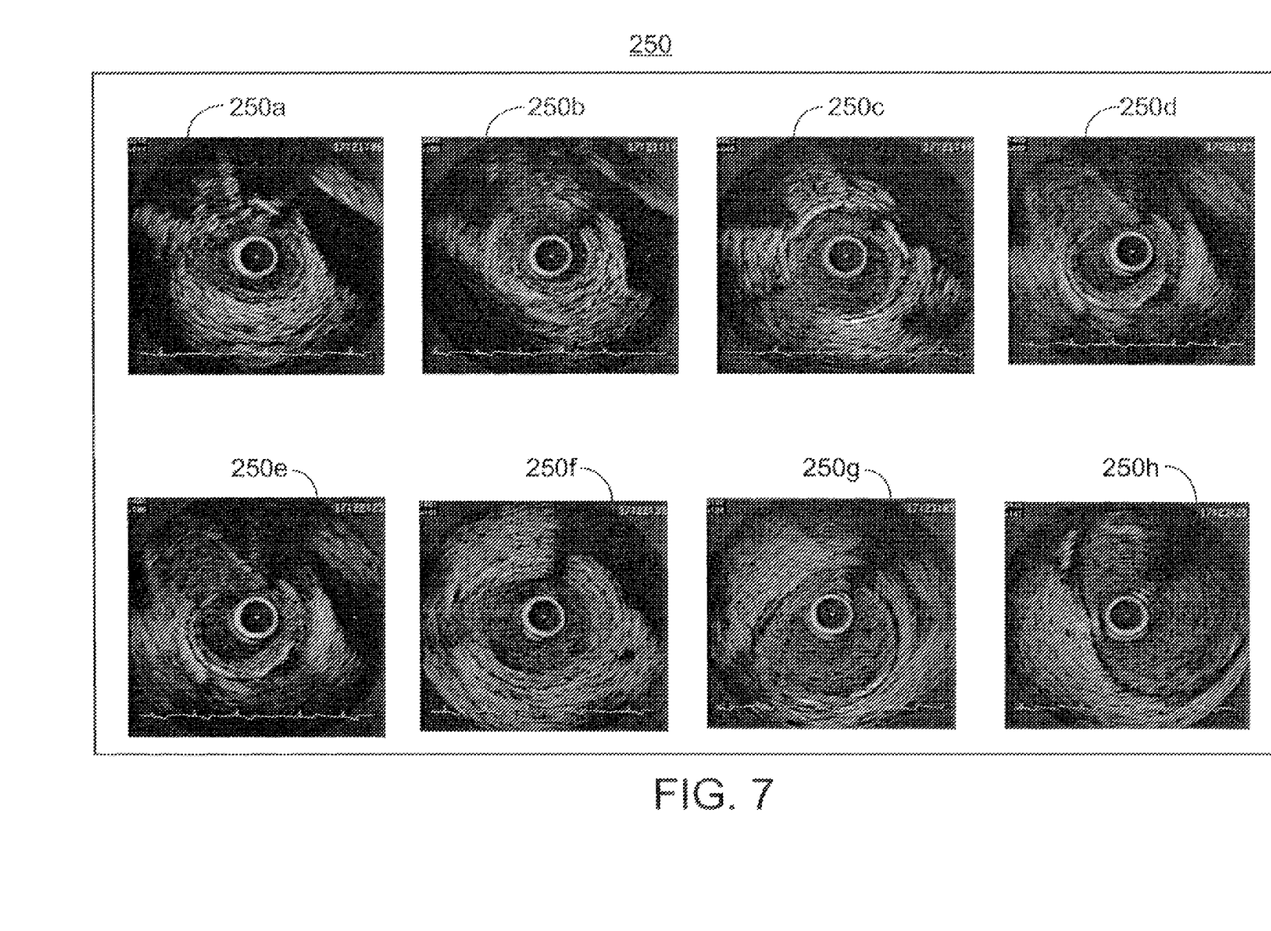
FIG. 7 shows a series of successive intravascular ultrasound (IVUS) images.
Figure 8:
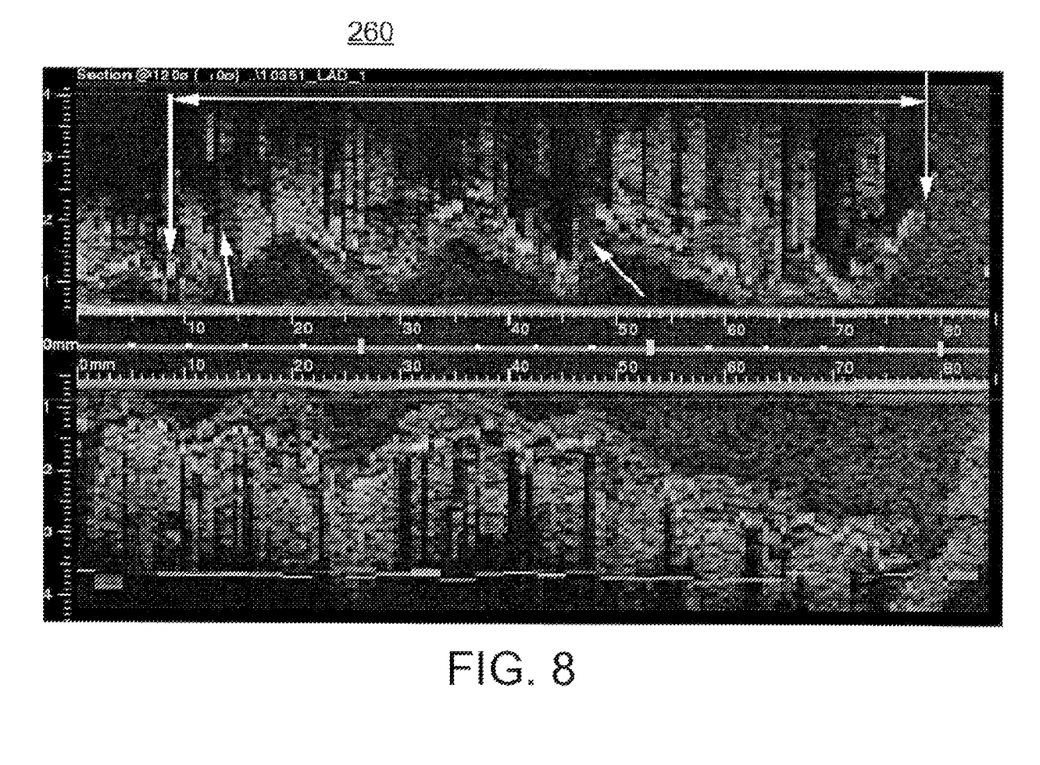
FIG. 8 shows a reconstruction of an arterial lumen from IVUS images.

FIG. 7 shows a series 250 of successive IVUS diastolic frames 250a-h of an artery. A reconstruction 260 of an arterial lumen obtained from stacking the successive IVUS frames 250a-h from FIG. 7 is shown in FIG. 8.

Figure 4C:
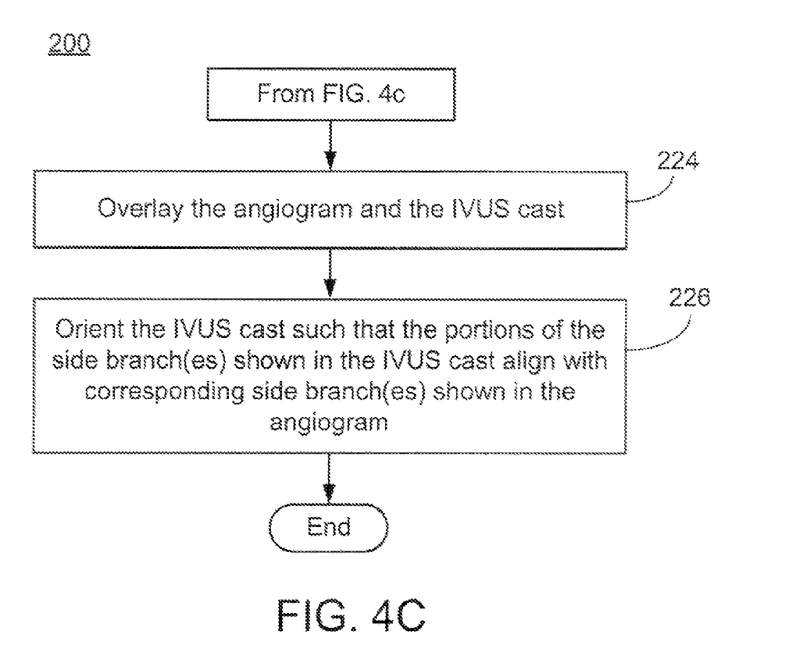
Figure 9:
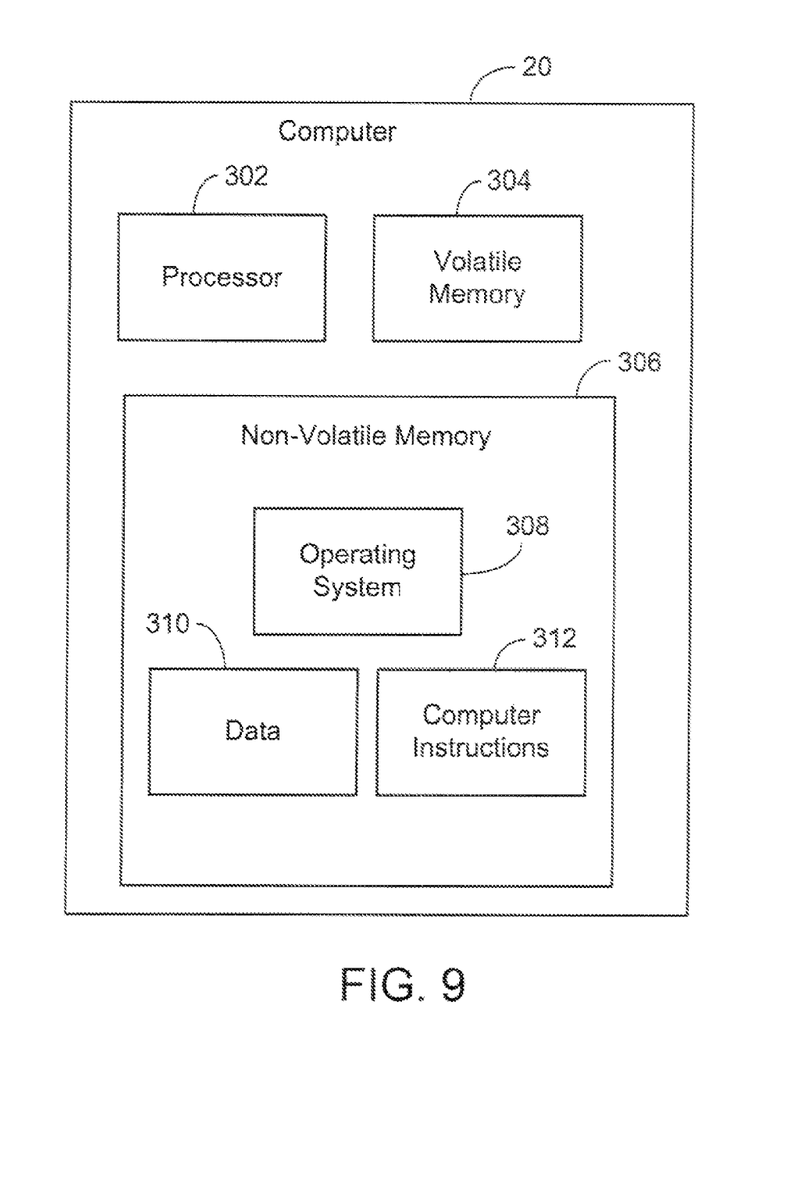
FIG. 9 shows a block diagram of a computer for use with the system of FIG. 1.

FIG. 9 shows a schematic diagram of the computer 20. The computer 20 includes a processor 302, a volatile memory 304, and a non-volatile memory 306 (e.g., hard disk). The non-volatile memory 306 stores instructions for implementing an operating system 308, data 310, and computer instructions 312 that are selective placed in the volatile memory 304 for execution by the processor 302 to perform one or more steps of the imaging process 200 described in FIGS. 4a-c.

The imaging process 200 is not limited to use with the hardware and software of FIG. 9 and may find applicability in any computing or processing environment and with any type of machine that is capable of running a computer program. The process 200 may be implemented, in part, in hardware, software, or a combination of the two. For example, one or more steps of the process 200 may be implemented in a circuit that includes one or a combination of a processor, a memory, programmable logic and logic gates. The process 200 may be implemented, in part, in computer programs executed on programmable computers/machines that each include a processor, a storage medium or other article of manufacture that is readable by the processor (including a volatile and non-volatile memory and/or storage elements), at least one input device, and one or more output devices. Program code may be applied to data entered using an input device to perform one or more steps of the process 200 and to generate output information.

Each such program may be implemented in a high level procedural or object-oriented programming language to communicate with a computer system. However, the programs can be implemented in assembly or machine language. The language may be a compiled or an interpreted language. Each computer program may be stored on a storage medium or device (e.g., CD-ROM, hard disk, flash memory or magnetic diskette) that is readable by a general or special purpose programmable computer for configuring and operating the computer when the storage medium or device is read by the computer to perform one or more steps of the process 200. The process 200 may also be implemented, at least in part, as a machine-readable storage medium, configured with a computer program, where upon execution, instructions in the computer program cause the computer to operate in accordance with the process 200.

The system and techniques applied above could be modified to use other catheter-based intravascular imaging procedures in place of IVUS. Examples of other such techniques include, but are not limited to OCT, NIR, and intravascular magnetic resonance imaging (MRI) systems. For example, the process 200 described above in FIGS. 4a-c, is not limited to IVUS images and may be used to determine the absolute spatial orientation of other intravascular images.

The process is not limited to the specific embodiments described herein. Nor is the process 200 limited to the specific processing order steps shown in FIGS. 4a-c. For example, the steps illustrated in FIGS. 4a-c may be reordered or removed, as necessary, to achieve the results set forth above. Other embodiments are within the scope of the following claims.

What is claimed is:

1. A method for imaging a blood vessel having a wall defining a lumen in a subject, the method comprising:
   guiding a transducer attached to a catheter inserted into the blood vessel to a first site within the blood vessel, wherein the first site is distal to a region of interest, the region of interest having a side branch joined to the wall;
   moving the catheter to a second site proximal to the first site at a speed selected to enable the transducer to generate a signal indicative of a geometry of the wall, the lumen, and a portion of the side branch;
   generating frames showing portions of the wall, the portions being located within the region of interest;
   reconstructing an image of the lumen of the blood vessel by stacking together successive frames to form a cast of the blood vessel;
   compensating for any relative rotation between successive images caused by bending or torsion of the catheter to produce a corrected cast of the blood vessel that is corrected for relative orientation;
   overlaying an angiogram and the corrected cast; and
   orienting the corrected cast such that the portion of the side branch in the corrected cast aligns with a corresponding portion of the side branch in the angiogram to provide an image of the blood vessel that is corrected for relative orientation and absolute orientation with respect to a coordinate system of the patient.

2. The method of claim 1, further comprising:
   while moving the catheter to the second site, directing energy from the transducer towards the wall of the blood vessel; and
   detecting, at the transducer, echoes resulting from energy reflected from the wall, the transducer generating the signal indicative of the geometry of the wall based on the echoes.

3. The method of claim 2, wherein directing energy comprises directing acoustic energy.

4. The method of claim 1, wherein reconstructing the image from the frames comprises:
   selecting a first subset of the frames, the first subset including frames acquired at times separated by an integer number of heart cycles; and
   stacking successive frames from the first subset to form the cast of the blood vessel.

5. The method of claim 1, wherein guiding a transducer comprises obtaining real-time angiograms showing at least a portion of the catheter inside the lumen.

6. The method of claim 1, wherein moving the catheter comprises:
   selecting the speed such that the signal includes information for generating at least one image showing a portion of the side branch.

7. The method of claim 1, where orienting the first image with the second image corrects an erroneous relative orientation between the first image and the second image caused by movement associated with moving the catheter.

8. A system for generating an image of a blood vessel having a wall in a subject, the system comprising:
   (a) a catheter-based imaging system comprising
      (i) a catheter for insertion into the blood vessel;
      (ii) a transducer secured to a distal end of the catheter and configured to generate a signal indicative of a geometry of the wall, a lumen defined by the wall, and a portion of a side branch joined to the wall; and
      (iii) an image circuit processor coupled to the transducer, wherein the image circuit processor is configured to generate one or more frames showing portions of the wall from the signal generated by the transducer, wherein at least one of the frames comprises an image of the portion of the side branch;
   (b) an angiography system configured to generate an angiogram of the blood vessel and the portion of the side branch of the blood vessel; and
   (c) a computer in data communication with the imaging system and the angiography system, wherein the computer is programmed to:
      reconstruct an image of the lumen of the blood vessel by stacking together successive imaging system frames to form a cast of the blood vessel;
      compensate for any relative rotation between successive imaging system frames caused by bending or torsion of the catheter to produce a corrected cast of the blood vessel that is corrected for relative orientation;
      overlay the angiogram and the corrected cast; and
      orient the corrected cast such that the portion of the side branch in the corrected cast aligns with a corresponding portion of the side branch in the angiogram to provide an image of the blood vessel that is corrected for relative orientation and absolute orientation with respect to a coordinate system of the patient.

9. The system of claim 8, wherein the transducer is further configured to:
   direct energy towards the wall of the blood vessel; and
   detect echoes resulting from the energy being reflected from the wall, the signal from the transducer being generated based on the echoes.

10. The system of claim 9, wherein the transducer comprises an acoustic transducer.

11. The system of claim 8, wherein the transducer is further configured to:
   rotate about a central axis of the catheter.

12. The system of claim 8, wherein the transducer comprises an array of piezoelectric elements disposed about the periphery of the catheter, the transducer being further configured to illuminate the wall with a rotating beam of energy.

13. The system of claim 8, wherein the imaging system comprises an input for receiving the second image from an angiograph, the second image showing a three dimensional cast of the luminal boundary of the blood vessel.

14. The system of claim 8, wherein the imaging system is further configured to:
   generate frames showing portions of the wall from the signal generated by the transducer;
   select a first subset of the frames, the first subset including frames acquired at times separated by an integer number of heart cycles; and
   stack successive frames from the first subset to form a cast of the blood vessel, the first image including the cast.

15. The system of claim 8, further comprising a controller configured to:
   guide the catheter through the blood vessel to a first site within the blood vessel, the first site being distal to the side branch; and
   move the catheter to a second site within the blood vessel at a speed selected to enable at least one image showing a portion of the side branch to be obtained from the signal generated by the transducer, the second site being proximal to the first site.

16. A computer readable storage device having stored thereon software for processing image data, the software comprising instructions for causing a computer to:

receive a signal generated by a transducer on a catheter inserted into a blood vessel in a subject, the signal being indicative of a geometry of a wall of the blood vessel, a lumen defined by the wall, and a portion of a side branch joined to the wall;

generate one or more frames showing portions of the wall from the signal generated by the transducer, wherein at least one of the frames comprises an image of the portion of the side branch;

receive an angiogram of the blood vessel and the portion of the side branch of the blood vessel generated by an angiography system;

compensate for an relative rotation between successive imaging system frames caused by bending or torsion of the catheter to produce a corrected cast of the blood vessel that is corrected for relative orientation;

overlay the angiogram and the corrected cast; and orient the corrected cast such that the portion of the side branch in the corrected cast aligns with a corresponding portion of the side branch in the angiogram to provide an image of the blood vessel that is corrected for relative orientation and absolute orientation with respect to a coordinate system of the patient.

17. The computer readable storage device of claim 16, wherein the software further comprises instructions that cause the computer to:

select a first subset of the frames, the first subset including frames acquired at times separated by an integer number of heart cycles; and stack successive frames from the first subset to form a cast of the blood vessel.

18. The computer readable storage device of claim 16, wherein the software further comprises instructions that cause the computer to:

operate a controller to cause the controller to:

guide the catheter through the blood vessel to a first site within the blood vessel, the first site being distal to the side branch; and move the catheter to a second site within the blood vessel at a speed selected to enable at least one image showing a portion of the side branch to be obtained from the signal generated by the transducer, the second site being proximal to the first site.

* * * * *

UNITED STATES PATENT AND TRADEMARK OFFICE
CERTIFICATE OF CORRECTION

| | |
|---|---|
| PATENT NO. | : 8,452,371 B2 |
| APPLICATION NO. | : 11/680977 |
| DATED | : May 28, 2013 |
| INVENTOR(S) | : Charles L. Feldman, Peter Stone and Ahmet U. Coskun |

It is certified that error appears in the above-identified patent and that said Letters Patent is hereby corrected as shown below:

On the Title Page, Item (57) in the Abstract, line 5, delete "wall," and insert -- of the wall, --.

Signed and Sealed this
Twentieth Day of August, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,452,371 B2 | Page 1 of 1 |
| APPLICATION NO. | : 11/680977 | |
| DATED | : May 28, 2013 | |
| INVENTOR(S) | : Charles L. Feldman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 634 days.

Signed and Sealed this
Sixth Day of January, 2015

Michelle K. Lee
*Deputy Director of the United States Patent and Trademark Office*